United States Patent [19]
Altadonna, Jr.

[11] Patent Number: 6,015,425
[45] Date of Patent: Jan. 18, 2000

[54] NASAL AIR FRESHENER FOR DENTAL PATIENTS

[76] Inventor: James Altadonna, Jr., 203 Whitewood Dr., Massapequa Park, N.Y. 11762

[21] Appl. No.: 09/208,525

[22] Filed: Dec. 9, 1998

[51] Int. Cl.[7] ........................................................ A61F 5/08
[52] U.S. Cl. ................ 606/204.45; 606/199; 128/206.11
[58] Field of Search ................ 606/199, 204.45; 128/207.13, 206.11

[56] References Cited

U.S. PATENT DOCUMENTS

| | | |
|---|---|---|
| 4,231,360 | 11/1980 | Zloczysti et al. . |
| 4,267,831 | 5/1981 | Aguilar ................ 128/203.14 |
| 4,303,648 | 12/1981 | Witzel et al. . |
| 4,445,508 | 5/1984 | Lake . |
| 4,606,912 | 8/1986 | Rudy et al. . |
| 4,846,170 | 7/1989 | Manalley et al. ................ 128/207.13 |
| 5,243,708 | 9/1993 | Vanuch . |
| 5,281,415 | 1/1994 | Suzuki et al. . |
| 5,392,773 | 2/1995 | Bertrand ................ 128/206.11 |
| 5,417,205 | 5/1995 | Wang ................ 128/207.13 |
| 5,503,167 | 4/1996 | Wilson et al. . |
| 5,538,013 | 7/1996 | Brannon . |
| 5,636,628 | 6/1997 | Barnum . |
| 5,636,629 | 6/1997 | Patterson, Jr. . |
| 5,697,105 | 12/1997 | White . |
| 5,740,798 | 4/1998 | McKinney . |
| 5,922,006 | 7/1999 | Sugerman ........................ 606/204.45 |

*Primary Examiner*—Michael Buiz
*Assistant Examiner*—Tan-Uyen Thi Ho
*Attorney, Agent, or Firm*—Alfred M. Walker

[57] ABSTRACT

An odor desensitizing intra-nasal clip for dental patients includes a bendable arcuate band extending between distal ends. The ends have odor-emitting pads affixed thereon. The band has an inner surface coextensive with the band, wherein the inner surface contacts the respective right and left sides of a user's nasal septum when the outer distal ends are inserted into a user's right and left nostrils, with the band wrapped around the lower distal end of the nasal septum. Preferably, the band has a pair of reverse curvatures near its outer distal ends, so that the reverse curvatures separate the ends from contact with the surface of the user's nasal septum. To mask dental odors during dental procedures, the intra-nasal clip has odor-emitting absorbent pads attached to its distal ends; with odorant absorbed therein.

11 Claims, 3 Drawing Sheets

NASAL AIR FRESHENER FOR DENTAL PATIENTS

FIELD OF THE INVENTION

The present invention relates to an odor-desensitizing intra-nasal clip for dental-patients.

BACKGROUND OF THE INVENTION

Dental patients often complain about foul odors associated with certain procedures. The source of the odor is generally acknowledged to be bacterial decay within the mouth due to high temperatures generated by the drilling of teeth. The present invention reduces or completely masks the unpleasant odors in a convenient and aggressive manner.

Nose clips are known, but they are generally used to hold the nostrils closed, as in swimming or surgical procedures, as discussed in U.S. Pat. No. 4,231,360 of Zloczysti, and U.S. Pat. No. 4,445,508 of Lake.

To reduce malodorous mouth odors, various formulations in the form of tablets, liquids, or other medicants are applied to the mucosol cavities of the user's mouth, such as disclosed in U.S. Pat. No. 4,303,648 of Witzel, U.S. Pat. No. 4,606,912 of Rudy, or U.S. Pat. No. 5,281,415 of Suzuki. But these cannot be applied during dental procedures, except by intermittent spraying or ingesting into the patient's mouth.

However, odor reducing filter masks are known, but these generally cover the whole face or the whole nose, 4s in U.S. Pat. No. 5,636,629 of Patterson for a filter mask Other odor reducing filter masks which cover the face or the nostrils of the nose include U.S. Pat. No. 5,392,773 of Bertrand and U.S. Pat. No. 5,740,798 of McKinney for filter masks that cover and mask the outer nostril end of the nose. Masks which cover the whole nose include U.S. Pat. No. 5,243,708 of Vanuch and U.S. Pat. No. 5,697,105 of White.

Moreover, U.S. Pat. No. 5,636,628 of Barnum discloses a mask to counteract odors that includes a cloth substrate covering the nose and mouth of the user, wherein the cloth substrate is held over the face by ear pieces which tie around the ears.

U.S. Pat. No. 5,538,013 of Brannon describes a mask with a scenting means. However, the mask of Brannon '013 covers at least the whole nose of the user.

In addition, U.S. Pat. No. 5,503,167 of Wilson et al. discloses a face shield covering the whole face of a user, wherein the user holds the face shield by gripping a mouthpiece between the user's teeth.

Furthermore, U.S. Pat. No. 4,267,831 of Aguilar and U.S. Pat. No. 5,417,205 of Wang describe nasal air filters and medicament dispenser devices, wherein two medication dispensing tubes are provided, one for insertion into each nostril. The problem with Aguilar '831 and Wang '205 is that the cylindrical outer surfaces of each tube completely block each nostril, thus increasing discomfort and preventing normal breathing through the nostrils.

However, these face coverings or nose covering masks are bulky and interfere with normal breathing during dental procedures.

OBJECTS OF THE INVENTION

It is therefore an object of the present invention to provide an odor-desensitizing intra-nasal clip for dental patients, which can be inserted in to the nasal passages.

It is another object of the present invention to provide a bendable arcuate band for dental patients having odor emitting pads affixed thereon.

It is also an object provide a convenient odor emitting nasal clip which is compact and comfortable to wear, without interfering with normal breathing during dental procedures.

It is yet another object of the present invention to provide an odor emitting band which is pleasant and comfortable to wear during dental procedures.

It is yet another object of the present invention to provide an odor emitting intra-nasal clip for contacting the respective right and left sides of a user's nasal septum during dental procedures.

It is another object of the present invention to provide for an odor-emitting intra-nasal clip with ends which are separated from contact with the surface of the user's nasal septum.

It is another object of the present invention to provide a nasal clip having odor-emitting pads with odorant absorbed there within.

It is yet another object of the present invention to provide an assembly of odor-emitting nasal clips in a plurality of attached, user-detachable sealed packaging pouches, wherein a single nasal clip is enclosed within each packaging pouch.

It is yet another object of the present invention to provide sterile packaging pouches for odor-emitting nasal clips with an odor and oxygen barrier.

It is another object of the present invention to provide packaging pouches for odor-emitting nasal clips with which can be torn off individually.

It is a further object of the present invention to alter a dental patient's exposure to foul odors during a dental procedure.

It is yet another object of the present invention to provide an odor-emitting nasal clip with a pleasant-smelling odorant.

It is yet another object of the present invention to provide an odor-emitting nasal clip which does not interfere with normal breathing through the nostrils of the nose.

It is yet another object of the present invention to improve over the disadvantages of the prior art.

SUMMARY OF THE INVENTION

In keeping with these objects and others which may become apparent, the present odor desensitizing intra-nasal clip for dental patients, includes a bendable arcuate band extending between its outer distal ends, wherein the ends having odor-emitting pads affixed thereon.

The band has an inner surface which is coextensive with the band. The inner surface contacts the respective right and left sides of a user's nasal septum when the distal ends of the nasal clip are inserted into a user's right and left nostrils, with the band wrapped around the distal end of the dental patient's nasal septum.

The band preferably includes a pair of reverse curvatures near its outer distal ends. The reverse curvatures separate the ends from contact with the surface of the user's nasal septum.

The intra-nasal clip has odor-emitting pads, such as a pair of absorbent pads attached to the outer distal ends of the nasal clip, with pleasant smelling odorant absorbed there within.

The coating may be a of soft material, such as fabric or soft synthetic plastics.

The intra-nasal clip is flexible, spring-like and semi-rigid, and is made of a flexible spring-like and semi-rigid material, such as aluminum or plastic.

The nasal clip should be preferably packaged in a sterile environment, such as in a plurality of attached, user-detachable sealed packaging pouches wherein a single nasal clip is enclosed within each packaging pouch. To retain freshness, each packaging pouch includes an odor and oxygen barrier.

To remove a packaged nasal clip, each packaging pouch has a weakening seam for facilitating user tear-off of individual packaging pouches as desired, such as perforations between each packaging pouch.

Furthermore, the odor emitting nasal clip of the present invention alters dental patient's exposure to foul odors during a dental procedure, by masking dental bacterial odors. The nasal clips are used by inserting each end into a respective nostril of the user, wherein the nasal clip is held in place within the nostrils of the user, by clamping against the nasal septum.

Therefore, the present invention includes a miniature air freshener designed to be attached to the distal end of the nasal septum. It applies a pleasant scent directly within the nostrils.

Such a convenient, inexpensive, and effective personal air freshener can have other applications besides the dental usage described above. There are several situations which expose practitioners to environments with intense vile odors. Examples of such occupational hazards include crime scene investigations, autopsies of decaying cadavers, and work associated with sewage systems.

BRIEF DESCRIPTION OF THE DRAWINGS

The present invention can best be understood in connection with the accompanying drawing, in which.

DETAILED DESCRIPTION OF THE PREFERRED EMBODIMENTS

Figure 1:
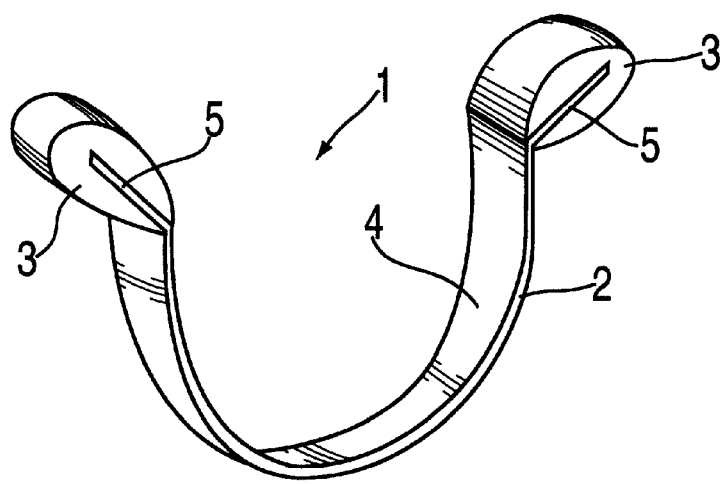
FIG. 1 is a perspective view of the nasal air freshener of the present invention.
Figure 2:
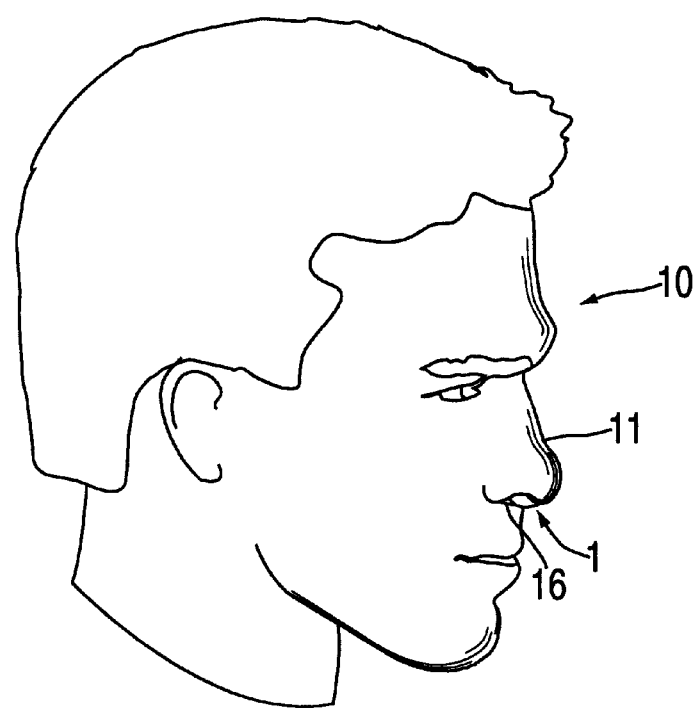
FIG. 2 is a side view of a facial profile of a user with air freshener of the present invention in use.

FIG. 1 shows nasal air freshener 1 of the present invention, which includes bendable frame 2 with distal frame ends 5 covered with absorbent pads 3. Inside surface 4 of frame 2 contacts the distal end of the nasal septum. When worn, (as shown in FIG. 2) nasal air freshener 1 is hardly visible, as shown worn by user 10 within nose 11. More importantly, nasal air freshener 1 does not protrude from the end of nose 11. This is important especially for dental procedures requiring the use of a cotton roll under the upper lip, since any protrusions of nasal filter coverings as in the prior art would interfere with the dentist's procedures and be uncomfortable for the patient.

Figure 3:
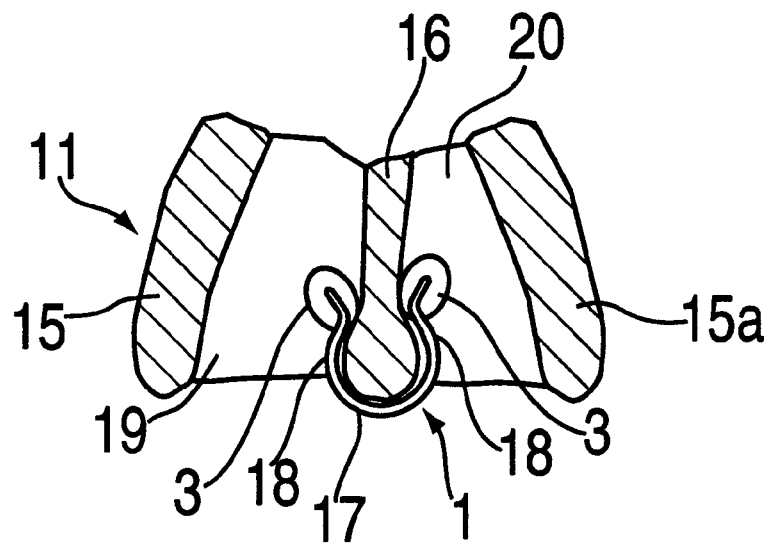
FIG. 3 is a front cross section detail of nasal passages showing the installation of the nasal air freshener of the present invention.

FIG. 3 is a cross sectional detail view showing the internal nasal passages with nasal air freshener 1 in place. Open nostrils 19 and 20 are formed between outer sides 15, 15a of nose 11 and nasal septum 16. Distal end 17 of nasal septum 16 is somewhat bulbous. Sides, 2a, 2b of frame 2 of nasal air freshener 1 are pressed together by the user so that they form neck 18, bending around end 17 of nasal septum 16 to retain nasal air freshener 1 in place.

Absorbent pads 3 are prominently positioned within the air flow within open nostrils 19 and 20 without significantly blocking these passages.

Figure 4:
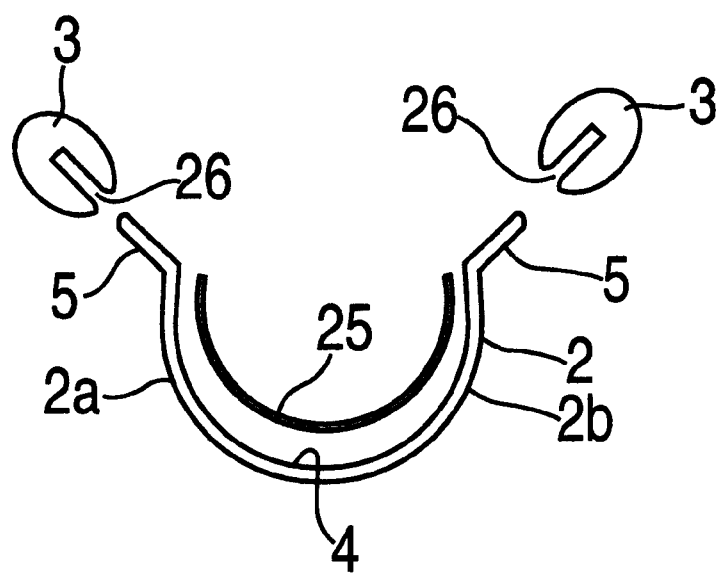
FIG. 4 is an exploded front elevational view of the nasal air freshener.

FIG. 4 shows an exploded view of nasal air freshener 1. The material of frame member 2 is preferably a flexible material, such as ductile aluminum, with very little spring temper. Frame number 2 is die cut and formed. If frame number 2 is then tumbled to remove any sharp edges, it can be used directly. A bendable plastic may be used as an alternative. Optionally, fabric layer 25 can be adhesively bonded to inside surface 4 of frame 2 as a more comfortable cushion against the sensitive skin of nasal septum end 17. Absorbent pads 3 are die cut from a cushion-like material such as a dense cotton felt or a semi-rigid polyurethane foam or similar material. Absorbent pads 3 are then adhesively bonded to frame ends 5 in recesses 26. Pads 3 are then adapted to support an odor emitting material such as by being dipped in a fragrant liquid during the manufacturing process. Alternatively, pads 3 maybe attached to an outer surface (not shown) of frame ends 5 by other conventional attaching means.

Unlike the prior art filter masks that cover the entire nostril opening or nose itself, air freshener 1 is an intra-nasal device which is inserted within nostril 19 and 20, not over nostrils 19 and 20.

Figure 5:
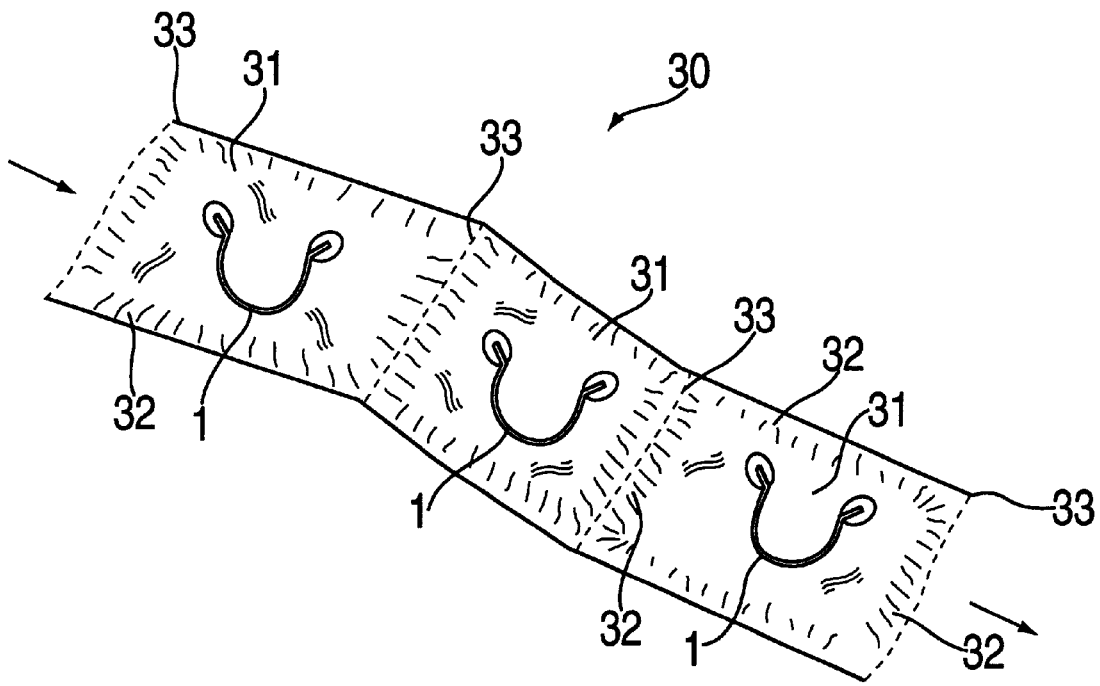
FIG. 5 is a perspective view of the nasal air freshener in preferred packaging and, FIG. 6 is side elevational view of a nasal air freshener clip in an alternate embodiment.
Figure 6:
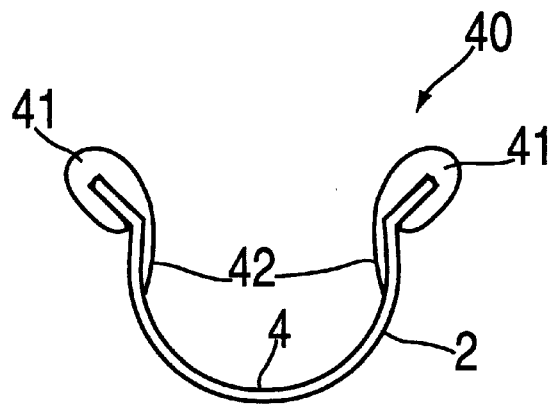

Although many alternatives are available for packaging of nasal air freshener 1 of the present invention, the preferred package is a heat sealed pouch as is commonly used for automobile air fresheners. Since the invention is of small dimensions, an automatic machine continuous belt package (as is often used for candy lollipops) would be most convenient, especially for a dental office. Such package 30 is shown in FIG. 5. Film material 31 can be a suitable packaging material, such as a polyester film of du Pont Corporation of Delaware. Material is automatically heat sealed at edges 32 and perforated at perforations 33 for easy tear-off, thus creating a number of odor and oxygen barriers which keep the scent of absorbent pads 3 enclosed and protect the active ingredient from oxidation.

Nasal air freshener 1 can be activated with a variety of scents. In addition, nasal air freshener 1 is very easy to apply and to remove, and is inexpensive to manufacture and package.

It is further noted that other modifications may be made to the present invention, without departing from the scope of the invention, as noted in the appended Claims.

I claim:

1. An odor desensitizing intra-nasal clip for dental patients, comprising:
    a bendable arcuate band extending between distal ends, said ends having odor-emitting means affixed thereon;
    said band having an inner surface coextensive with said band, said inner surface for intra-nasal contacting the respective right and left sides of a user's nasal septum, when said distal ends are inserted into a user's right and left nostrils with said band wrapped around the distal end of the nasal septum;
    said band having a pair of reverse curvatures near said respective distal ends, said reverse curvatures providing for separation of said ends from contact with the surface of the user's nasal septum.

2. The intra-nasal clip of claim 1 wherein said odor-emitting means comprises a pair of absorbent pads attached to said distal ends; said pads having an odorant absorbed therewithin.

3. The intra-nasal clip of claim 2 wherein said inner surface is provided with a coating of soft material.

4. The intra-nasal clip of claim 3 wherein said soft material comprises fabric.

5. The intra-nasal clip of claim 4 wherein said band is comprised of aluminum.

6. The intra-nasal clip of claim 4 wherein said band is comprised of plastic.

7. An assembly of a plurality of attached, user-detachable sealed packaging pouches wherein a respective single unit of said intra-nasal clip is enclosed within each respective packaging pouch.

8. The assembly of claim 7 wherein said packaging pouches comprise an odor and oxygen barrier.

9. The assembly of claim 8 wherein said respective packaging pouches have weakening means for facilitating user tear-off of individual packaging pouches as desired.

10. The assembly of claim 9 wherein said weakening means comprises perforations between respective packaging pouches.

11. A method of altering a dental patient's exposure to foul odors during a dental procedure, comprising the steps of:

affixing absorbent pads to the ends of a soft, bendable arcuate band having two ends and a reverse curvature near each respective end;

impregnating said absorbent pads with a pleasant-smelling odorant;

inserting said ends of said band into the nostrils of the dental patient;

wrapping said band around the end of the dental patient's nose;

gently pressing said band into contact with the right and left sides of the inner nasal septum of the user, for grasping contact therebetween;

ensuring that said reverse curvatures near said ends cause separation between the surface of the user's nasal septum and said odorant pads; and removing said intra-nasal clip at the end of the dental procedure or sooner if desired.

* * * * *